(12) United States Patent
Huss et al.

(10) Patent No.: US 11,896,708 B2
(45) Date of Patent: Feb. 13, 2024

(54) SYNERGISTIC ANTIOXIDANT COSMETIC COMPOSITION CONTAINING AT LEAST ONE HYDROXYTYROSOL AND AT LEAST ONE SULFORAPHANE

(71) Applicant: Barnet Products, LLC, Englewood Cliffs, NJ (US)

(72) Inventors: Nickolas Huss, Maywood, NJ (US); Yiming Lu, Weehawken, NJ (US); Rossana Lanza, Glen Rock, NJ (US)

(73) Assignee: Barnet Products LLC, Englewood Cliffs, NJ (US)

(*) Notice: Subject to any disclaimer, the term of this patent is extended or adjusted under 35 U.S.C. 154(b) by 143 days.

(21) Appl. No.: 17/480,687

(22) Filed: Sep. 21, 2021

(65) Prior Publication Data
US 2022/0087925 A1    Mar. 24, 2022

Related U.S. Application Data

(60) Provisional application No. 63/082,198, filed on Sep. 23, 2020.

(51) Int. Cl.
*A61K 8/9789*    (2017.01)
*A61K 8/34*    (2006.01)
(Continued)

(52) U.S. Cl.
CPC ............ *A61K 8/9789* (2017.08); *A61K 8/345* (2013.01); *A61Q 1/00* (2013.01); *A61Q 5/02* (2013.01);
(Continued)

(58) Field of Classification Search
None
See application file for complete search history.

(56) References Cited

U.S. PATENT DOCUMENTS

| 7,261,909 B2 * | 8/2007 | Crea | A01N 31/16 424/769 |
| 2004/0202684 A1 * | 10/2004 | Djerassi | A61Q 19/08 424/401 |

(Continued)

FOREIGN PATENT DOCUMENTS

| CN | 101516364 B | 12/2011 | |
| EP | 1844666 A1 * | 10/2007 | ............. A23D 9/007 |
| KR | 101905009 B1 * | 10/2018 | |

OTHER PUBLICATIONS

English language translation of KR 101905009 B1 (2018). (Year: 2018).*

(Continued)

*Primary Examiner* — Dominic Lazaro
(74) *Attorney, Agent, or Firm* — Keith D. Nowak; Danielle C. Sullivan; Carter Ledyard & Milburn LLP

(57) ABSTRACT

This invention illustrates a composition which has a high antioxidant power in cosmetic products. The composition includes a combination of two critical ingredients, originating from two natural superfood products: olive and kale. This current technology utilizes the sprout of kale, instead of the whole plant, as one ingredient. In the perspective of olive extract, it is either in the form of a concentrated liquid syrup of olive tree and leaf, which is enriched with natural polyphenols, especially with high content of hydroxytyrosol, or in the form of pure liquid hydroxytyrosol. An enhanced antioxidant power is observed when incorporating the kale sprouts together with the olive leaf extract.

17 Claims, 3 Drawing Sheets

(51) Int. Cl.
  *A61Q 1/00* (2006.01)
  *A61Q 5/02* (2006.01)
  *A61Q 5/12* (2006.01)
  *A61Q 17/04* (2006.01)

(52) U.S. Cl.
  CPC ............... *A61Q 5/12* (2013.01); *A61Q 17/04* (2013.01); *A61K 2800/48* (2013.01); *A61K 2800/522* (2013.01); *A61K 2800/591* (2013.01)

(56) References Cited

U.S. PATENT DOCUMENTS

| | | |
|---|---|---|
| 2007/0202195 A1 | 8/2007 | Wang et al. |
| 2017/0189326 A1 | 6/2017 | Perricone et al. |
| 2017/0274007 A1 | 9/2017 | Terenzio et al. |
| 2018/0291210 A1 | 10/2018 | Sarkas et al. |

OTHER PUBLICATIONS

Eurol BT Product Data Sheet, Hallstar Beauty, May 2020 https://www.hallstarbeauty.com/webfoo/wp-content/uploads/Functional-Naturals-Eurol-BTEnglish-i.pdf.

Mehta et al. "Cytoprotective Effects of Natural Compounds against Oxidative Stress", Oct. 20, 2018, pp. 1-20, vol. 7, 147, Antioxidants, Switzerland.

* cited by examiner

SYNERGISTIC ANTIOXIDANT COSMETIC COMPOSITION CONTAINING AT LEAST ONE HYDROXYTYROSOL AND AT LEAST ONE SULFORAPHANE

This application claims priority to U.S. Provisional Patent Application No. 63/082,198 filed Sep. 23, 2020, entitled "SYNERGISTIC ANTIOXIDANT COSMETIC COMPOSITION CONTAINING AT LEAST ONE HYDROXYTYROSOL AND AT LEAST ONE SULFORAPHANE," which is hereby incorporated by reference herein.

BACKGROUND OF THE INVENTION

There has been an on-going trend to include food related ingredients in the cosmetic industry in recent years. It therefore generates the concept of "feeding the skin". This convergence of both food and cosmetics significantly encourages the community to find new opportunities and generate new ingredients and resources for existing cosmetic products and applications. One of the avenues for including food ingredients in cosmetics is to use superfoods, which supply various nutritional needs for everyday consumption.

The present invention is related to the composition of two highly functional superfood ingredients which are particularly enriched in polyphenols and sulforaphane, olive and kale sprout. This composition has the potential to be used as antioxidant, anti-inflammatory, and anti-aging raw material in cosmetic compositions.

Kale and other Brassicaceae vegetables, such as cabbage, radish, broccoli, etc. are highly enriched with antioxidants and vitamins. One of the phytochemicals named sulforaphane, belonging to the derivatives of glucosinolates, is unique to this genus. Various research has shown potential anti-inflammatory and skin-repair efficacy of sulforaphane in vitro, by enhancing the inherent protection mechanism owned by multicellular organisms. It mediates and induces the gene coding of cytoprotective proteins via the Keap 1-Nrf2-antioxidant response element pathway, and thus regulates and reduces skin sensitivity to UV inflicted damage. These results indicate that sulforaphane is able to relieve oxidative stress and prevent skin-aging. Even though mature kale vegetable has a content of sulforaphane, the sprout of kale has a higher content than the mature plants. This enables a more ideal application of sprout than mature plants with a higher antioxidant potential.

It is well-known in the Mediterranean region that consuming foods containing olive and its related produce can lower the incidence of coronary heart disease and cancer. The major phyto-compounds derived from the olive tree, such as hydroxytyrosol, tyrosol and oleuropein, preserve high antioxidant power due to the presence of phenolic structure, as radical scavenger. In particular, there is a significant chemoprotective effect of hydroxytyrosol on damaged skin, induced by UV exposure. It reduces the DNA strand breaks and thus prevents the DNA damage provoked by oxidative stress. In addition, hydroxytyrosol has anti-inflammatory activities. It inhibits inflammatory swelling and hyperalgesia. It also suppresses proinflammatory cytokine in animal models.

Currently there are very few examples exploring the use of kale sprout in combination with olive extract for cosmetic ingredients. This invention demonstrates a composition with both kale sprouts and olive tree/leaf extract, with the capability to reduce skin inflammation, assist skin-repair, and provide strong protection for skin.

SUMMARY OF THE INVENTION

Disclosed herein is a composition composed of two major superfood ingredients or their extracts, solvent/co-solvent, and a thickening agent. Specifically, two superfood ingredients are olive tree/leaf extract and kale sprout. Both ingredients have high antioxidant power and are beneficial to skin. The composition presented in this invention is not limited or restricted to use in any cosmetic formulations with a certain range of use level. These cosmetic formulations are majorly in forms of skin care products but not limited to lipstick, lip balm, foundation, sunscreens, bath and shower gels, shampoos, conditioners, hair spray, cream, moisturizer, lotion, cleanser and shaving products.

In one preferred embodiment, the olive tree/leaf extract is in two forms. One is a viscous liquid syrup, which has a typical characteristic fruity aroma. This syrup is not oil soluble but highly water soluble. The other form is the liquid of pure hydroxytyrosol. According to the invention, the syrup of olive tree/leaf contains large amount of hydroxytyrosol, oleuropein, tyrosol and other polyphenol derivatives.

In a preferred embodiment of the invention, the concentration of the hydroxytyrosol in the liquid syrup has a range from 0.01% to 25%.

In another preferred embodiment of the invention, liquid hydroxytyrosol has a purity higher than 99.5%.

In another preferred embodiment, the kale sprout is milled into dry powder as solid particles, and it is neither water soluble nor oil soluble.

In a preferred embodiment, the kale sprout powder has specific particle size, which is no more than 38 μm, as it passes through a round mesh screen with mesh count at 400.

According to the invention, the kale sprout powder contains high levels of sulforaphane, and it is extracted with water at room temperature.

In a preferred embodiment of the invention, the ppm concentration of sulforaphane in the kale sprout powder ranges from 1 ppm to 8000 ppm.

According to the invention the composition requires several processing steps to be completed. One step is to pre-mix the solid powder with deionized water to extract the water-soluble compounds into an aqueous phase. In the next step, the whole mixture is filtered through filter papers or filter bags to remove the solid kale sprout particles, as solid waste. The filtrate solution is used as stock solution in the following steps, when adding other ingredients.

According to the invention, several other cosolvent are used to formulate this composition.

In a preferred embodiment, the cosolvent is selected from the diols, triols and polyols. To be specific, 1,3-propanediol and glycerin are the representative cosolvents in the composition. However, the cosolvent can be selected from ethylene glycol, propylene glycol, butylene glycol, hexylene glycol but not limited to other liquid-state diols, triols or even polyols.

According to the invention, a thickening agent is used as viscosity modifier.

In a preferred embodiment, the thickening agent is chosen from the following polysaccharide such as starch, carboxymethylcellulose, hydroxyethylcellulose, carrageenan, alginate/alginic acid, pectin, konjac gum, locust bean gum or other thickeners which are plant derived. In a preferred embodiment, the thickening agent in the composition is xanthan gum.

According to the invention, the composition given in this patent demonstrates a high antioxidant power over a long period of time, proven by analytical test with oxygen free-radical scavenger. In addition, there is a synergistic effect (enhancement) on the antioxidant power when combing kale sprout powder with the olive leaf extract.

In a preferred embodiment, the composition presented in this patent is not limited or restricted to use in any cosmetic formulations with a certain range of use level.

BRIEF DESCRIPTION OF THE DRAWINGS

As shown in FIG. 2, kale sprout shows synergistic effect on the AP power when combining with olive leaf extract. For Composition A without olive leaf extract, but with only kale sprout, the AP power is equal to 0 (zero).

As shown in FIG. 3 Composition A has higher AP power than BHT powder.

DETAILED DESCRIPTION OF THE INVENTION

Figure 1:
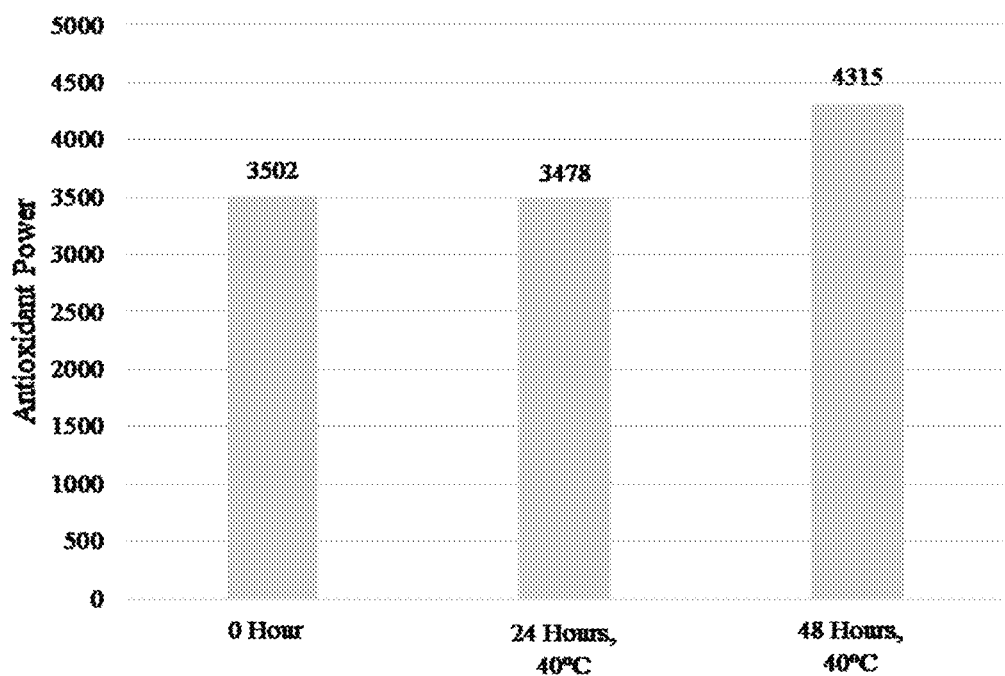
FIG. 1 is a bar graph showing Antioxidant Power (AP power) of Composition A using the ESR method. The AP power at 0 hour is measured as received. For the AP power at 24 hours and 48 hours, the sample is incubated at 40° C. and measured after cooling down to room temperature (~25° C.).

The composition presented in this invention offers two opportunities: First, it enables the inclusion of superfood as potential efficacious functional ingredients for cosmetic raw material. Second, seed sprouts (dried and milled into a powder), especially from the genus of Brassicaceae are utilized to boost the antioxidant activities of other natural products with high content of polyphenols.

In a preferred embodiment of this invention, one superfood candidate is chosen from the genus of Brassicaceae vegetables. The common examples of these vegetables are horseradish, cabbage, brussels sprouts, broccoli, cauliflower, mustard green, turnip, and radish. Specifically, kale, broccoli, radish, mustard green and brussels sprouts have sulforaphane in high concentration, and sulforaphane is known to be a powerful natural antioxidant.

In another preferred embodiment of this invention, one of the several following sprout powders is selected as the major ingredient, such as the sprout powder of kale, broccoli and radish. Comparing to the mature plant of kale, broccoli and radish, seed sprouts of these plants have higher sulforaphane content. Particularly, sprout powder of kale is used in this invention due to the high sulforaphane content, which can reach up to 8000 ppm.

In one preferred embodiment of this invention, olive leaf extract is selected as another source of potential superfood ingredient. The olive leaf extract is in two forms. One is an amber/brown syrup, and it is highly enriched with polyphenols. One of the most important traits of this syrup is that it has high content of hydroxytyrosol, which is a powerful antioxidant and a beneficial active for skin. Concentration of the hydroxytyrosol is as high as 25% and the total amount of polyphenol concentration is over 40%. The other form is the liquid hydroxytyrosol. In a preferred embodiment of this invention, the purity of the liquid hydroxytyrosol is higher than 99.5%.

According to the invention, the composition consists of four major parts: two antioxidants, solvent/cosolvent, and a thickener. No extra preservatives or preservative systems are utilized due to the high amount of cosolvent, which is resistant to bacteria and fungi. The preservation ability against bacteria and fungi is tested via both the water activity test, and the micro-challenge test.

In a preferred embodiment, one superfood ingredient is sprout powder of kale, and the concentration is ranged from 0.1% to 5%. In another preferred embodiment, the other superfood ingredient is olive leaf extract, in the form of syrup. The concentration is ranged from 0.1% to 5%.

In another preferred embodiment, pure hydroxytyrosol is used as a replacement of syrup. The concentration of the hydroxytyrosol is in between 0.005% to 0.5%.

In another preferred embodiment, the major solvent is water and the concentration is inbetween 10% to 50%. The cosolvent is a combination of 1,3-propanediol and glycerine. The concentration is in between 5% to 40%.

In another preferred embodiment, the concentration of the polysaccharide thickener, xanthan gum, is in between 0.1% to 0.5%. This composition is designated as Composition A, which will be referred in the following context.

According to the invention, two major steps are required to successfully achieve formulating Composition A. In the first step, it includes an extraction of water-soluble content from sprout powder of kale, with a filtration. In the second step, all other ingredients will be added sequentially into the filtrated stock solution.

Examples

The following non-limiting examples are provided for illustration purposes in order to discuss/investigate the antioxidant power of Composition A. The results are discussed based on analytical test.

Figure 2:
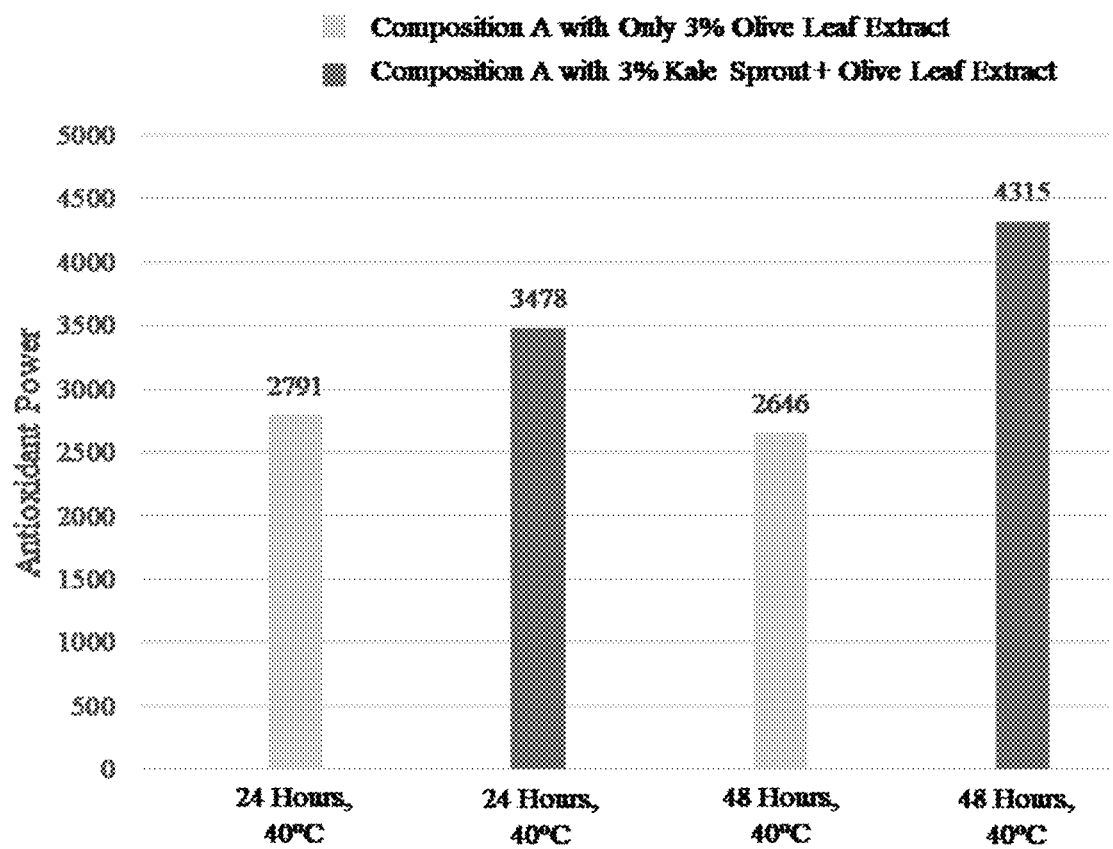
FIG. 2 is a bar graph showing Antioxidant Power (AP power) of Composition A with or without kale sprout at 24 hours and 48 hours. The samples are incubated at 40° C. and measured after cooling down at room temperature (~25° C.).
Figure 3:
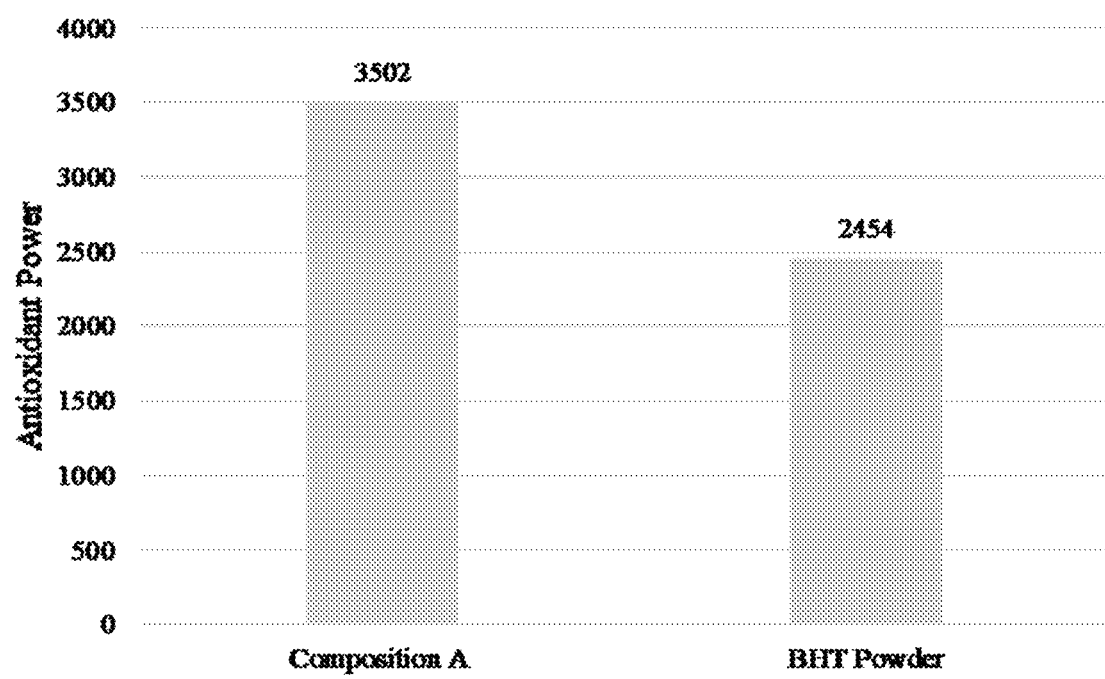
FIG. 3 is a bar graph showing Antioxidant Power (AP power) of Composition A and BHT powder using ESR method. The AP power is measured as received.

Antioxidant power (AP) of Composition A is determined by electron spin resonance (ESR) spectroscopy. Similar to other antioxidant capacity measurement, 1,1-diphenyl-2-picryl-hydrazil (DPPH) radical is used. However, ESR spectroscopy is a more favored method than traditional colorimetric/UV-Vis spectrometric method due to that the measurement is irrelevant to the sample color as well as sample turbidity. The antioxidant power is represented by antioxidative units (AU), where 1 AU corresponds to the activity of a 1 ppm solution of Vitamin C benchmark. Based on the results, the antioxidant power of Composition A with a 3% usage of olive leaf extract has an AU number at 3500. In the meantime, long term stability of the AP is also tested at elevated temperature at 40° C. after 24 hours and 48 hours of incubation. The data shows that the AP value of Composition A remains unchanged and maintained in the range of 3500 to 4500, independent of temperature or incubation time (FIG. 1). When in absence of sprout powder (kale), the AP value is significant lower at elevated temperature after 24 hours and 48 hours of incubation. This indicates that the kale sprout powder shows a synergistic effect on increasing the AP value of olive leaf extract, at elongated time and elevated temperature (FIG. 2). The antioxidant power of composition A is also tested against wildly used synthetic antioxidant-butylated hydroxytoluene (BHT). The AP value of Composition A is approximately 40% higher than BHT (FIG. 3), commonly used in cosmetic product. The results indicate that Composition A has the potential as an antioxidant for skin protection.

Stability evaluation of composition A is done by incorporation with an oil-in-water (O/W) emulsion base. However, the cosmetic formulation base is not limited to any formulation based on the purpose of final application. The formula of the O/W emulsion is illustrated in the following table:

| INCI Name | % w/w |
|---|---|
| Phase A | |
| Caprylic Triglyceride | |
| Hydrogenated Lecithin | |
| Stearyl Alcohol | |
| Behenyl Alcohol | 1.00 |
| Phytosterols Glyceryl Stearate | |
| Polyglyceryl-1 Myristate | |
| Tocopherol | |
| Cetyl Alcohol | 0.50 |
| Batyl Alcohol | 0.70 |
| Simmondsia Chinensis Seed Oil | 4.00 |
| Phase B | |
| Polyacrylic acid sodium salt | 0.2 |
| Water | 81.47 |
| Glycerin | 5 |
| Phase C | |
| Phenoxyethanol | 0.40 |
| Phase D | |
| Arginine 10% a.q. | 0.73 |
| Isopentyldiol | 5.00 |
| Composition A | 1.00 |

Procedure:
1. The ingredients of phase A are combined and heated at 80° C. Mix at 150 rpm with propeller mixer until all solid particles dissolve.
2. The ingredients of phase B are combined and heated up to 80° C. Mix at 3000 rpm under homogenizer for 30 mins when forming a uniform and consistent water phase.
3. Adding mixture of phase A into phase B at 80° C. and mix at 4000 rpm under homogenizer for 30 mins.
4. Slowly cool down the homogenized emulsion (after step 3) below 40° C. with sweeping blade mixing at 150 rpm.
5. Add phase C and keep mixing with sweeping blade for 5 mins at 150 rpm.
6. Add ingredients in phase D, one by one and keep mixing with sweeping blade for 10 mins at 150 rpm.
7. The final pH of the formulation should be in between pH 5 to 5.5. Adjust the pH of final formulation with arginine (10% a.q.) until the pH falls into the desirable range.

Stability of the above emulsion with 1% Combination A is evaluated at three different temperatures at 25° C., 45° C. and 55° C. The incubation time in 25° C. and 45° C. is 2 months. At 55° C., it only lasts for one month. The emulsion is consistent at all temperature with good stability. Due to the presence of the polyphenol content, when temperature elevated at 45° C. and 55° C., there is a color change of the emulsion base. For the 25° C. sample, the color change is not significant. Composition A should always be post added into the final formulation. In addition, Composition A is both pH sensitive and temperature sensitive due to the presence of polyphenols. When post-adding composition A into the final cosmetic formulation, it should strictly follow the recommended pH (no higher than pH 5.5) and below 40° C. Storage of the composition or the final cosmetic formulation should be at room temperature. Following similar formulation guidelines, composition A is also incorporated into two other cosmetic bases. One is a clear carbomer gel and the other is a lecithin-based emulsion. The antioxidant power of both bases with composition A is evaluated by ESR spectroscopy. The data is consistent and indicates that composition A is not only able to endow base formulation with significant antioxidant power but also retain its antioxidant power in different bases with a long-term stability.

The invention claimed is:

1. A composition consisting of: (i) olive tree/leaf extract; (ii) kale extract; (iii) water, diols, triols, polyols or combinations thereof; and (iv) a polysaccharide thickening agent.

2. The composition according to claim 1 wherein said kale extract is in the form of sprout powder; and wherein said olive tree/leaf extract is in the form of a liquid syrup, or in the form of hydroxytyrosol.

3. The composition according to claim 2 wherein said olive syrup is highly enriched with polyphenols.

4. The composition according to claim 3 wherein said polyphenols are hydroxytyrosol, tyrosol and oleuropein.

5. The composition according to claim 2 wherein said olive syrup contains at least 25% hydroxytyrosol.

6. The composition according to claim 2 wherein said hydroxytyrosol has a purity higher than 99.5%.

7. The composition according to claim 2 wherein said kale sprout powder enhances the antioxidant power of the olive leaf/tree extract in the form of the liquid syrup or the hydroxytyrosol.

8. The composition according to claim 2, wherein concentration range of the sprout powder is 0.1% to 5%.

9. The composition according to claim 1 wherein said water is deionized.

10. The composition according to claim 1 wherein said diols, triols and polyols are selected from ethylene glycol, 1,2-propanediol, 1,3-propanediol, 1,4-butanediol, hexylene glycol and glycerine.

11. The composition according to claim 1, wherein said composition provide cosmetic bases with antioxidant power.

12. The composition according to claim 11, wherein said antioxidant power is the same at room temperature.

13. The composition according to claim 11, wherein said antioxidant power does not change at elevated temperature and does not change over time.

14. The composition according to claim 1, wherein said composition shows higher antioxidant power than butylated hydroxytoluene (BHT).

15. The composition according to claim 1, wherein said composition can be used in a range of cosmetic products, in the form of a lotion, a cream, a gel, a spray, a foam, a solid stick, a shampoo, a hair conditioner, a lacquer, a make-up or a sunscreen.

16. The composition according to claim 1, wherein the concentration of sulforaphane from the kale extract ranges from 1 ppm to 8000 ppm.

17. The composition according to claim 1, wherein the polysaccharide thickening agent is xanthan gum.

* * * * *